United States Patent [19]

Bottaccio et al.

[11] 4,132,732

[45] Jan. 2, 1979

[54] PROCESS FOR PREPARING ALPHA-FORMYL ACIDS

[75] Inventors: Giorgio Bottaccio; Stefano Campolmi; Maria G. Felicioli, all of Novara, Italy

[73] Assignee: Montedison S.p.A., Milan, Italy

[21] Appl. No.: 882,867

[22] Filed: Mar. 2, 1978

[30] Foreign Application Priority Data

Mar. 3, 1977 [IT] Italy .............................. 20857 A/77

[51] Int. Cl.$^2$ ............................................ C07C 65/02
[52] U.S. Cl. .................................. 562/550; 562/423; 260/413
[58] Field of Search ........... 260/526 R, 526 N, 521 R, 260/520 R, 535 R

[56] References Cited

U.S. PATENT DOCUMENTS

| | | | |
|---|---|---|---|
| 3,798,266 | 3/1974 | Bottaccio | 260/526 R |
| 3,912,778 | 10/1975 | Alneri | 260/535 P |
| 3,976,677 | 8/1976 | Bottaccio | 260/526 R |
| 4,032,555 | 6/1977 | Bottaccio | 260/526 R |
| 4,052,461 | 10/1977 | Tinker | 260/526 R |

FOREIGN PATENT DOCUMENTS

| | | | |
|---|---|---|---|
| 2245892 | 3/1973 | Fed. Rep. of Germany | 260/535 P |
| 803120 | 10/1958 | United Kingdom | 260/526 |

*Primary Examiner*—Paul J. Killos

[57] ABSTRACT

Alpha-formyl acids are prepared by carboxylation of aldehydes in the presence of unsubstituted or substituted alkaline phenates, and of aprotic organic solvents.

9 Claims, No Drawings

PROCESS FOR PREPARING ALPHA-FORMYL ACIDS

THE PRIOR ART

The known carboxylation techniques, particularly those involving the carboxylation with $CO_2$ of substrates containing activated hydrogen atoms do not contemplate the possibility of introducing $CO_2$ in alpha-position in respect to aldehyde groups.

In particular, so far as applicants are aware, methods of carboxylating aldehydes with $CO_2$ in a basic medium are not known in the art.

THE PRESENT INVENTION

One object of this invention is to provide a simple and economical process for preparing alpha-formyl acids and derivatives thereof.

This and other objects are achieved by the invention in accordance with which alpha-formyl acids having the general formula

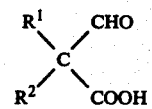

in which
R[1] and R[2], which may be the same or different, each represents H, linear or branched-chain alkyls containing from 1 to 20 carbon atoms, linear or branched-chain alkenyls containing from 2 to 20 carbon atoms, aryls, substituted aryls, phenoxy groups, acyloxy groups, or alkyloxy derivatives containing from 1 to 20 carbon atoms,
are prepared by reacting an aldehyde of the formula:

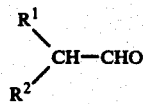

in which
R[1] and R[2] have the same significance as in formula (I) with $CO_2$ in the presence of alkaline phenates and of an aprotic organic solvent, the molar ratio of all alkaline phenate to aldehyde being from about 0.5:1 to 4:1, and the reaction being carried out at a temperature of from about 0° C. to about 80° C., for from 0.1 to 3 hours.

The alpha-formyl acids or semi-aldehydes (I) obtained by the process of the invention have known uses, including use as particularly reactive intermediates, for example in the dye industry. Of particular interest is malonic semi-aldehyde which is obtainable from acetic aldehyde which, by conventional synthesis operations, can result in malonic and malic acids which are known to be useful in various industrial fields, such as in the food industry. etc.

The semi-aldehydes (I) are normally difficult to prepare due to their instability; for example, the malonic semi-aldehyde has only been prepared previously by heating malic acid with $H_2SO_4$ or by more complex methods.

The aldehydes (II) which have been carboxylated successfully by the present method include acetic aldehyde, n-butyric aldehyde, isobutyric aldehyde, capronic aldehyde, 2-phenyl-propionic aldehyde, and citronellal.

The phenates useful in the process of the invention are alkaline salts of phenols having the general formula

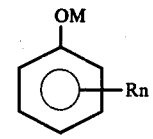

in which
R is hydrogen, linear or branched-chain alkyl containing from 1 to 20 carbon atoms, or a phenyl or alkoxy group;
M is an alkaline metal; and
n is an integer from 1 to 5.

Specifically useful phenates include the sodium or potassium salts of phenol, of ortho- and para-cresol, of 2,6-di-tert.butyl-para-cresol, and of hydroquinone, the sodium and potassium salts of phenol being presently preferred.

A variety of aprotic organic solvents are useful in the present process, including amides such as dimethylformamide and hexamethylphosphotriamide; sulphoxides such as dimethylsulphoxide, phosphoric esters, glymes (or dimethyl ethers of polyethylene glycols), ethers, cyclic ethers such as tetrahydrofuran, esters such as ethylene methylether acetate; aliphatic amines such as triethylamine; cyclic and aromatic amines such as beta-picoline; and hydrocarbons such as benzene.

The specific phenate selected for use in the process can depend on the solvent selected. Thus, when the solvent is a low polar solvent such as a hydrocarbon, it is preferable to employ sterically hindered phenates in the phenate-solvent coupling.

The carboxylation conditions according to this invention permit achievement of a high selectivity and include temperatures of from about 0° C. to about 80° C., preferably from 10° C. to 20° C.; reaction times of from about 0.1 to about 3 hours; and phenate/substrate molar ratios of from about 0.5:1 to about 4:1.

Unless the foregoing conditions are observed, the desired introduction of the carboxylic group in alpha position with respect to the aldehyde function either does not occur (as in fact the known prior art indicates) or it occurs in an unsatisfactory manner with low selectivities.

The present process represents an unexpected advance in view of the negativism of the prior art as to the possibility of carboxylation with $CO_2$ and alkaline phenates of organic substrates, since the prior art indicates that such technology is not practically applicable to aldehyde-functioned substrates, such indication having resulted in a clear prejudice, for those skilled in the art, against such a practically useful process involving the use of $CO_2$ and aldehydes of formula (II).

According to a practical embodiment of the invention, the process is carried out as follows:
the solvent and alkaline phenate, after blow-off of air, are introduced under a $CO_2$ head and at the selected temperature, into a thermoregulated reactor equipped with a stirrer, a thermometer, and a $CO_2$ proportioning device. The aldehyde, dissolved in the solvent, is then introduced into the reactor, under stirring. After the predetermined reaction time in the range given herein, the reaction product is separated by acidification with mineral acids, e.g., $H_2SO_4$, extraction with a solvent such as ethyl ether, and neutralized with an aqueous alkaline carbonate, e.g., sodium carbonate. From the aqueous phase containing the alkaline salt of the semi-aldehyde thus obtained, the pure alpha-formyl acid is obtained by acidification of said aqueous phase with dilute inorganic acids, e.g., $H_2SO_4$, extraction with solvents, crystallization, washing, etc.

The simplicity of the operations involved in the present process are particularly advantageous. Another advantage resides in the high yield and purity of the products obtained, which is of considerable importance for use of the products as intermediates in the preparation of fine chemicals.

The following examples are given to illustrate the process of the invention in more detail and are not intended to be limiting.

EXAMPLE 1

Into a thermoregulated 250 cc reactor, equipped with a stirrer, a thermometer and a $CO_2$ inlet pipe, 20 g of potassium O-cresolate in 75 cc of tetrahydrofuran were introduced after blow-off of the air and under a $CO_2$ head, the absorption being carried on for half an hour at a temperature of 20° C. Under stirring and in a time-period of 5 minutes, 7.0 g of capronic aldehyde dissolved in 5 cc of tetranydrofuran were introduced into the reactor and the reaction was allowed to proceed at 20° C. for 15 minutes.

The reaction mixture was gradually poured into a 400 cc beaker containing 40 cc of ether, 40 cc of a 10% sulphuric acid solution, cooled down to 0° C. The ether layer was drawn off and the aqueous residue was treated three times with 30 cc of cold ethyl ether each time. The other layer and the three extracts, after having been collected together, were treated with 30 cc of a 10% solution of sodium carbonate. The drawn-off ether layer was further extracted with 2 portions of 20 cc each of 10% sodium carbonate. The aqueous phases collected together and containing the sodium salt of the semialdehyde corresponding to the starting aldehyde were divided into two equal portions.

A conventional quantitative analysis with hydroxylamine conducted on the first portion revealed a CO percentage corresponding to 4.6 g of sodium salt of the semialdehyde (carboxylation yield equal to 40%).

The residual ether phase, after extraction with carbonate, revealed, on gas-chromatographic analysis, 4.2 g of unreacted capronic aldehyde and 14.4 g of O-cresolate. The reaction selectivity was about 100%.

The second portion of the extraction of the ether layer with 20 cc of 10% sodium carbonate was brought to a pH of about 2 with 50 cc of a cold 10% solution of sulphuric acid. The aqueous phase was extracted with 3 portions of ether of 30 cc each. The ether extracts were introduced into a rotary evaporator operating under vacuum and at low temperature. The resulting oily residue crystallized after a few hours to a white solid product which, after repeated washings with petroleum ether, exhibited a melting point of 55°-60° C. and a simultaneous loss of $CO_2$.

The product was identified through its 2,4-dinitrophenylhydrazone (melting point = 84°-85° C.) as alpha-formyl-capronic acid.

By operating as described herein, employing a reaction time of 3 hours and a temperature of 50° C., 0.8 g of sodium salt of alpha-formyl capronic acid was obtained. Carboxylation yields: about 7%. Selectivity: 7.7%.

EXAMPLE 2

Into a thermoregulated 1000 cc reactor, equipped with a stirrer, a thermometer and an inlet pipe for $CO_2$, and after blow-off of air, 20 g of potassium O-cresolate in 75 cc of tetrahydrofuran were introduced under a $CO_2$ head, the absorption being carried on for half an hour at a temperature of 20° C. Under stirring, and in a time-period of about 5 minutes, 2.75 g of acetic aldehyde dissolved in 25 cc of tetranydrofuran were introduced and allowed to react at 20° C. for 15 minutes.

At the conclusion of the reaction, the reaction mass was cooled to 0° C. and, controlling the temperature, a suspension of 15 g of 2,4-dinitrophenylhydrazine in 400 cc of 10% $H_2SO_4$ was gradually added thereto. The mass was stirred at room temperature for about 1 hour. The mixture was then extracted three times with 500 cc of ether each time, and the ether extracts were treated with 3 portions each of 200 cc of 10% $Na_2CO_3$.

The resulting ether phase, evaporated to dryness in a rotary evaporator, left an orange residue of 11.5 g. Said residue was found to be 2,4-dinitrophenyl-hydrazone of acetic aldehyde (melting point = 113°-115° C.).

The alkaline aqueous phase of the preceding operations was brought to an acid pH with 400 cc of 10% $H_2SO_4$. Finally it was extracted with three portions of ether of 500 cc each. The ether extracts, after evaporation of dryness in a rotary evaporator, left a red-orange solid residue weighing 2.9 g, which proved to be 2,4-dinitrophenyl hydrazone of alpha-formyl-acetic acid deriving from the carboxylation of acetaldehyde (melting point = 190°-192° C.). Carboxylation yield = 18%.

EXAMPLES 3 TO 6

Operating according to the modalities and molar ratios as in Example 1 and employing, as phenate, sodium O-cresolate on different aldehyde substrate, the results recorded in Table I were obtained.

TABLE I

| Ex. No. | Starting Aldehyde | Acid Obtained | Carboxylation Yields % | Reaction Time Minutes |
|---|---|---|---|---|
| 3 | $CH_3CH_2CH_2CHO$ | $CH_3CH_2\underset{\underset{COOH}{|}}{\overset{\overset{CHO}{|}}{CH}}$ | 8 | 30 |
| 4 | $\underset{CH_3}{\overset{CH_3}{\diagdown}}CH-CHO$ | $\underset{CH_3}{\overset{CH_3}{\diagdown}}\underset{}{\overset{\overset{CHO}{|}}{C}}-COOH$ | 45 | 30 |

TABLE I-continued

| Ex. No. | Starting Aldehyde | Acid Obtained | Carboxylation Yields % | Reaction Time Minutes |
|---|---|---|---|---|
| 5 | Ph-CH(CH₃)-CHO | Ph-C(CH₃)(CHO)(COOH) | 1-2 | 30 |
| 6 | citronella CH₃-C(CH₃)=CH-CH₂-CH₂-CH(CH₃)-CH₂-CHO | * | 40 | 30 |

* CH₃-C(CH₃)=CH-CH₂-CH₂-CH(CH₃)-CH(COOH)-CHO with CH₃ branch

EXAMPLES 7 TO 12

Operating according to the modalities and molar ratios as in Example 1, the carboxylation of isobutyric aldehyde, carried out by employing various alkaline phenates, gave the results recorded in Table II.

TABLE II

| Ex. No. | Phenol | Alkaline Metal | Carboxylation Yields % | Reaction Time Minutes |
|---|---|---|---|---|
| 7 | phenol (OH) | Na | 33 | 30 |
| 8 | phenol (OH) | K | 43 | 15 |
| 9 | o-cresol (OH, CH₃) | Na | 45 | 30 |
| 10 | o-cresol (OH, CH₃) | K | 48 | 30 |
| 11 | 2,6-di-t-butyl-4-methylphenol | Na | 10 | 30 |
| 12 | hydroquinone (HO—⌬—OH) | Na | 19 | 30 |

EXAMPLES 13 TO 21

Operating according to the modalities and molar ratios of Example 1 and employing, in the carboxylation of isobutyric aldehyde, various phenate/solvent systems, the results recorded in Table III were obtained.

TABLE III

| Ex. No. | Phenate | Solvent | Carboxylation Yields % | Reaction Time Minutes |
|---|---|---|---|---|
| 13 | PhONa | dimethylformamide | 57 | 30 |
| 14 | o-cresolate-ONa | benzene | 3 | 30 |
| 15 | o-cresolate-ONa | tetrahydrofuran | 45 | 30 |
| 16 | o-cresolate-ONa | β-picoline | 11 | 30 |
| 17 | PhONa | CH₃COO—CH₂—CH(OCH₃)—CH₂ | 5 | 30 |
| 18 | PhONa | hexamethylphosphotriamide | 27 | 30 |
| 19 | PhONa | dimethylsulphoxide | 7 | 30 |
| 20 | o-cresolate-ONa | dimethyl ether of diethylene glycol | 56 | 30 |
| 21 | o-cresolate-ONa | triethylamine | 11 | 30 |

EXAMPLES 22 TO 30

Operating according to the modalities of Example 1, but varying the reaction conditions and the molar ratios between the reagents, the results recorded in Table IV were obtained from the carboxylation of isobutyric aldehyde with sodium O-cresolate in tetrahydrofuran.

TABLE IV

| Ex. No. | Temperature °C | Reaction Time Minutes | O-cresolate/aldehyde Molar Ratio | Carboxylation Yields % |
|---|---|---|---|---|
| 22 | 10 | 30 | 1:1 | 24 |
| 23 | 25 | 30 | 1:1 | 28 |
| 24 | 50 | 30 | 1:1 | 5.5 |
| 25 | 25 | 5 | 1:1 | 28 |
| 26 | 25 | 60 | 1:1 | 10 |
| 27 | 25 | 180 | 1:1 | 11 |
| 28 | 25 | 30 | 0.5:1 | 11 |
| 29 | 25 | 30 | 2:1 | 45 |
| 30 | 25 | 30 | 3:1 | 58 |

EXAMPLE 31

A thermoregulated 250 cc reactor, equipped with a stirrer, a thermometer and a CO₂ inlet pipe, was charged, after blowing off of air, with 31 g of sodium O-cresolate in 70 cc of β-picoline under a CO₂ head, the absorption being carried on for half an hour at a temperature of 20° C. Under stirring, and in a time of about 5 minutes, 2.2 g of acetic aldehyde dissolved in 7 cc of β-picoline were introduced into the reactor, whereupon the reaction was allowed to proceed for 15 minutes, at 20° C.

At the conclusion of the reaction, the reaction mass was cooled to 0° C. and 40 cc of H₂O were gradually added, while controlling the temperature. The resulting aqueous suspension containing the sodium salt of α-formyl-acetic acid was then introduced into a thermoregulated 250 cc reactor equipped with a stirrer, a thermometer, a dropping funnel and a reflux cooler. By means of the dropping funnel, 5 cc of HCN were gradually added. The mixture, which reacted during this operation and for a successive 2 hours, was kept at 0°-5° C. Subsequently, always at the same temperature, 60 cc of 50% H₂SO₄ were added, bringing the pH to a value of about 1–2; the temperature was then raised to the boiling point of the mixture and maintained at that boiling temperature for about 2 hours.

At the conclusion of that operation, from the aqueous phase, cooled down to room temperature, 20 cc of solution were drawn off for analysis, and put in a distillation apparatus consisting of a 100 cc flask, a connecting tube with thermometer, a Liebig cooler and a distillate collecting drum.

0.22 g of adipic acid (gas-chromatographic reference standard) and 50 cc of n-butyl alcohol were added to the flask. About 60 cc of water/n-butanol azeotrope were then distilled and the residue in the flask was subjected to gas-chromatographic analysis. It revealed a peak which, by the mass spectrum, was identified as butyl ester of malic acid corresponding to 0.82 g by weight of product.

In the foregoing Examples percentages are by weight unless otherwise stated.

What is claimed is:

1. A process for preparing alpha-formyl acids having the general formula (I):

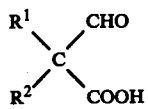

in which
R¹ and R², which may be the same or different, each represents a hydrogen atom, a linear or branched-chain alkyl containing from 1 to 20 carbon atoms, linear or branched chain alkenyls containing from 2 to 20 carbon atoms, aryl, substituted aryl, a phenoxy group, an acyloxy group or alkoxyl having from 1 to 20 carbon atoms,
which process comprises reacting an aldehyde of the general formula (II):

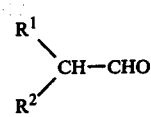

in which R¹ and R² have the same significance as in general formula (I) with CO₂, in the presence of alkaline phenates in a molar ratio of phenate to aldehyde of from about 0.5:1 to about 4:1 and of an aprotic organic solvent, at a temperature of from 0° C. to 80° C., and for from 0.1 to 3 hours.

2. The process of claim 1, in which the reaction is carried out at a temperature of from about 10° C. to about 20° C.

3. The process of claim 1, in which the reaction time is from about 0.1 hour to about 0.5 hour.

4. The process of claim 1, in which the alkaline phenates consist of alkaline metal salts of phenols having the formula:

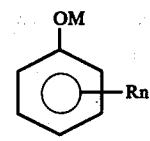

wherein R is a hydrogen atom or a linear or branched-chain alkyl containing from 1 to 20 carbon atoms, a phenyl, or an alkoxy group, M is the alkaline metal, and n is an integer from 1 to 5.

5. The process of claim 4, in which the alkaline phenates are sodium or potassium salts of the phenol.

6. The process of claim 1, in which the starting aldehyde is selected from the group consisting of acetic aldehyde, n-butyric aldehyde, isobutyric aldehyde, capronic aldehyde, 2-phenyl-propionic aldehyde, and citronellal.

7. The process of claim 6, in which the starting aldehyde is acetic aldehyde.

8. The process of claim 1, in which the solvent is selected from the group consisting of amides, sulphoxides, phosphoric esters, dimethyl ethers of polyethylene glycols, ethers, cyclic ethers, esters, aliphatic, cyclic and aromatic amines and hydrocarbons.

9. The process of claim 8, in which the solvent is selected from the group consisting of tetrahydrofuran, dimethylformamide, benzene, β-picoline, ethylene methylether acetate, hexamethyl-phosphotriamide, dimethylsulphoxide, diethylene glycol dimethylether and triethylamine.

* * * * *